(12) United States Patent
Matsumoto

(10) Patent No.: US 9,406,459 B2
(45) Date of Patent: Aug. 2, 2016

(54) BIOLOGICAL INFORMATION MEASUREMENT DEVICE

(75) Inventor: Toshiki Matsumoto, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 494 days.

(21) Appl. No.: 14/117,065

(22) PCT Filed: May 10, 2012

(86) PCT No.: PCT/JP2012/003053
§ 371 (c)(1),
(2), (4) Date: Nov. 12, 2013

(87) PCT Pub. No.: WO2012/157220
PCT Pub. Date: Nov. 22, 2012

(65) Prior Publication Data
US 2015/0162146 A1 Jun. 11, 2015

(30) Foreign Application Priority Data
May 13, 2011 (JP) ................. 2011-108005

(51) Int. Cl.
*H01H 9/54* (2006.01)
*A61B 5/15* (2006.01)
(Continued)

(52) U.S. Cl.
CPC ............. *H01H 9/54* (2013.01); *A61B 5/1411* (2013.01); *A61B 5/14532* (2013.01);
(Continued)

(58) Field of Classification Search
CPC ............. A61B 5/1411; A61B 5/14532; A61B 5/150022; A61B 5/150358; A61B 2560/0209; A61B 2562/0295; A61B 5/157; H01H 9/54; H01H 2300/22; Y10T 307/977

USPC ......................................... 307/143
See application file for complete search history.

(56) References Cited

U.S. PATENT DOCUMENTS 7,737,581 B2 * 6/2010 Spurlin ............... A61M 5/1723
307/66
8,395,363 B2 * 3/2013 Matsumura .......... A61B 5/1411
315/209 CD
(Continued)

FOREIGN PATENT DOCUMENTS

JP 64-075738 A 3/1989
JP 2001-525588 A 12/2001
(Continued)

OTHER PUBLICATIONS

International Search Report for Application No. PCT/JP2012/003053 dated Aug. 14, 2012.
(Continued)

*Primary Examiner* — Rexford Barnie
*Assistant Examiner* — Elim Ortiz
(74) *Attorney, Agent, or Firm* — Pearne & Gordon LLP

(57) ABSTRACT

A biological information measurement device of the present invention includes: measurement unit (7) connected to sensor mounting unit (4); control unit (8) connected to measurement unit (7); power source switch (14) interposed between control unit (8) and power source (13); and power source switch drive circuit (11) connected to sensor mounting unit (4). One-shot pulse circuit (12) is interposed between sensor mounting unit (4) and power source switch drive circuit (11), and power source switch drive circuit (11), which is driven by an output of one-shot pulse circuit (12), opens and closes power source switch (14).

5 Claims, 6 Drawing Sheets

(51) Int. Cl.
*A61B 5/145* (2006.01)
*A61B 5/157* (2006.01)

(52) U.S. Cl.
CPC .... *A61B 5/150022* (2013.01); *A61B 5/150358* (2013.01); *A61B 5/157* (2013.01); *A61B 2560/0209* (2013.01); *A61B 2562/0295* (2013.01); *H01H 2300/022* (2013.01); *Y10T 307/977* (2015.04)

(56) References Cited

U.S. PATENT DOCUMENTS

| | | | |
|---|---|---|---|
| 9,087,149 B2 * | 7/2015 | Galley | G06F 19/3462 |
| 2009/0177117 A1 * | 7/2009 | Amano | A61B 5/1411 |
| | | | 600/583 |
| 2010/0219769 A1 | 9/2010 | Matsumura et al. | |
| 2014/0134655 A1 * | 5/2014 | Elder | G06F 19/10 |
| | | | 435/14 |

FOREIGN PATENT DOCUMENTS

| | | |
|---|---|---|
| JP | 2007-225615 A | 9/2007 |
| JP | 2008-246176 A | 10/2008 |
| JP | 2010-217074 A | 9/2010 |
| WO | 2009/047918 A1 | 4/2009 |

OTHER PUBLICATIONS

Notice of Allowance issued for JP Application No. 2013-514982 dated Feb. 3, 2015.

* cited by examiner

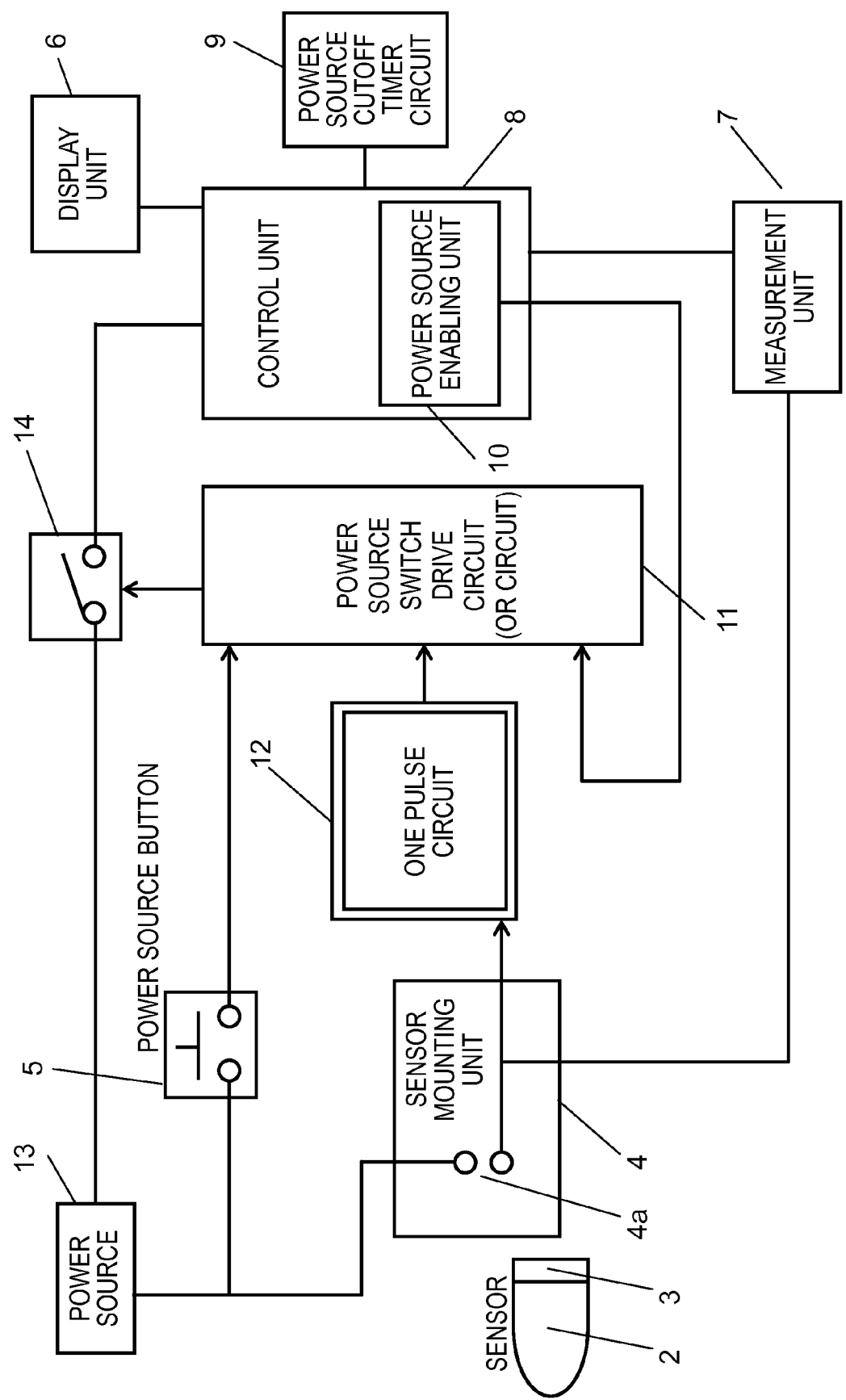

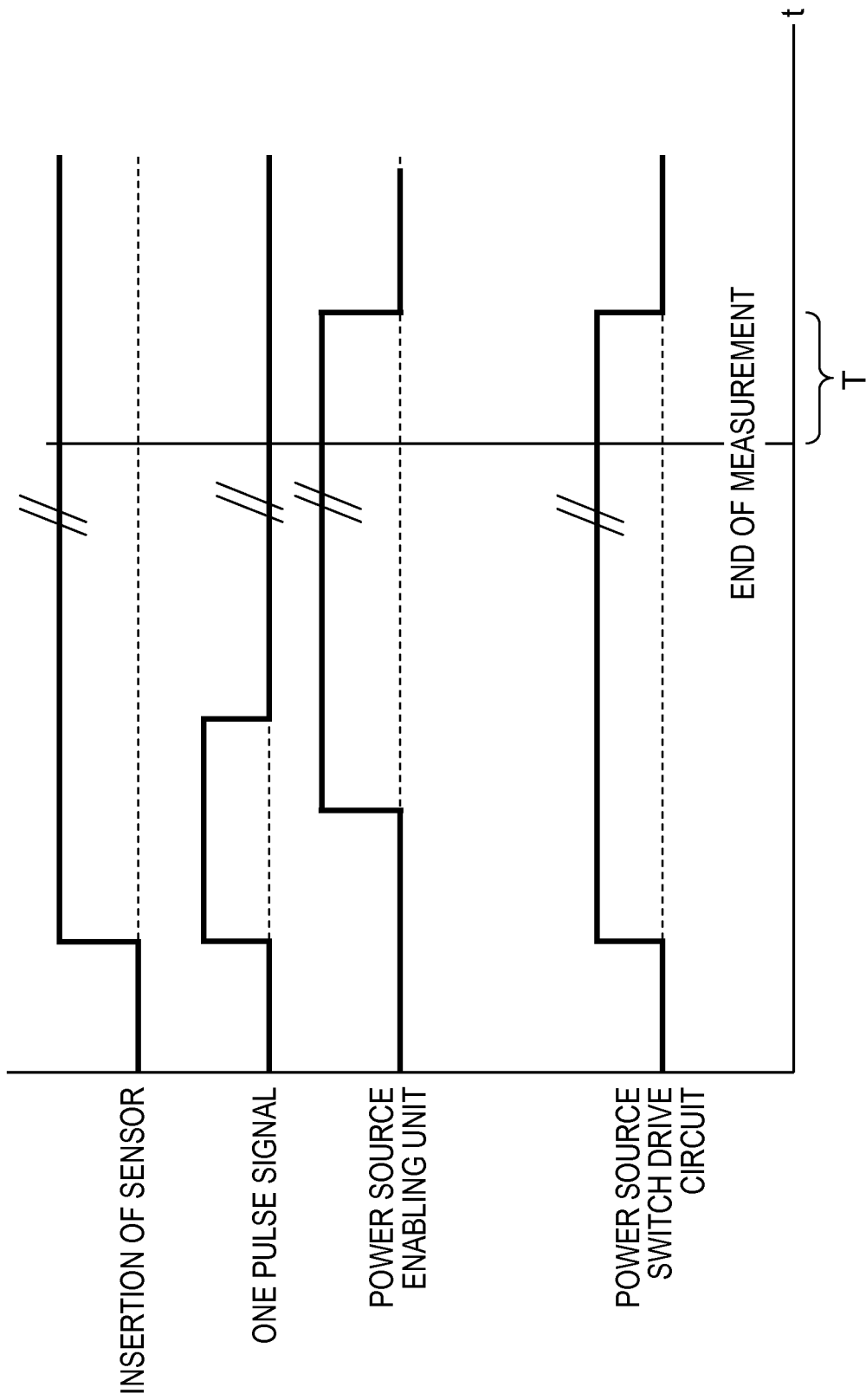

BIOLOGICAL INFORMATION MEASUREMENT DEVICE

TECHNICAL FIELD

The present invention relates to a biological information measurement device for measuring biological information, such as a blood glucose level, from blood.

BACKGROUND ART

Conventionally, such a biological information measurement device includes a measurement unit connected to a sensor mounting unit, a control unit connected to the measurement unit, and a display unit connected to the control unit (for instance, see Patent Literature 1).

In the conventional biological information measurement device, a blood glucose level sensor which is an example of a biological information measurement sensor is mounted into the sensor mounting unit, the control unit wakes up from an idle state, and the measurement unit can measure a blood glucose level. Thereafter, when a fixed time elapses while the blood glucose level sensor is left mounted into the sensor mounting unit, time-out is determined to set the control unit into the idle state for suppressing power consumption.

However, to return from the idle state (or a sleep state), power is supplied from a power source to the control unit. After all, power consumption occurs.

In other words, in the conventional biological information measurement device, when the sensor is left mounted into the sensor mounting unit after measurement of the blood glucose level, the control unit is set into the idle state (or the sleep state), but to return from the idle state (or the sleep state), power is continuously supplied from the power source to the control unit. After all, power consumption occurs.

This state will be briefly described now. For instance, when a large liquid crystal or the like is provided to enhance convenience, a scale of an electric circuit is increased, and to drive the large-scale electric circuit, a DC-DC converter (not shown) is provided in control unit 8. When power is supplied to the DC-DC converter (not shown) in control unit 8 in the "sleep mode", great power consumption of, for example, 100 μA to 200 μA occurs.

Accordingly, an object of the present invention is to prevent unintended power consumption from occurring.

CITATION LIST

Patent Literature

PTL 1: Japanese Published Patent Publication No. 2001-525588

SUMMARY OF THE INVENTION

A biological information measurement device of the present invention includes: a body case having a sensor mounting unit; a measurement unit connected to the sensor mounting unit; a control unit connected to the measurement unit; a display unit connected to the control unit; a power source supplying power to the control unit; a power source switch interposed between the control unit and the power source; and a power source switch drive circuit connected to the sensor mounting unit. A one-shot pulse circuit is interposed between the sensor mounting unit and the power source switch drive circuit, and the power source switch drive circuit, which is driven by an output of the one-shot pulse circuit, opens and closes the power source switch.

This can prevent unintended power consumption from occurring.

That is, in the present invention, the one-shot pulse circuit is interposed between the sensor mounting unit and the power source switch drive circuit, and when a sensor is mounted into the sensor mounting unit, the one-shot pulse circuit outputs a one pulse signal to the power source switch drive circuit only once. The one pulse signal drives the power source switch drive circuit to turn on the power source switch interposed between the control unit and the power source so that power supply from the power source to the control unit is started.

When the sensor is mounted into the sensor mounting unit, the one pulse signal is outputted to the power source switch drive circuit only once. Therefore, after the one pulse signal is outputted, a mounted state of the sensor cannot affect the power source switch drive circuit.

Therefore, even when the sensor is left mounted into the sensor mounting unit after measurement of a blood glucose level, the power source switch drive circuit can automatically turn off the power source switch. This can completely cut off power supplied from the power source to the control unit. That is, unlike the conventional sleep mode, power cannot be continuously supplied to the DC-DC converter in the control unit.

As a result, power is not supplied from the power source to the control unit, so that unintended power consumption can be prevented from occurring.

BRIEF DESCRIPTION OF DRAWINGS

FIG. 2 is a control block diagram of the biological information measurement device according to the first exemplary embodiment of the present invention.

FIG. 4 is an operation explanatory view of the essential part of the biological information measurement device according to the first exemplary embodiment of the present invention.

DESCRIPTION OF EMBODIMENT

Hereinafter, a biological information measurement device according to a first exemplary embodiment of the present invention will be described with reference to the accompanying drawings.

First Exemplary Embodiment

Figure 1:
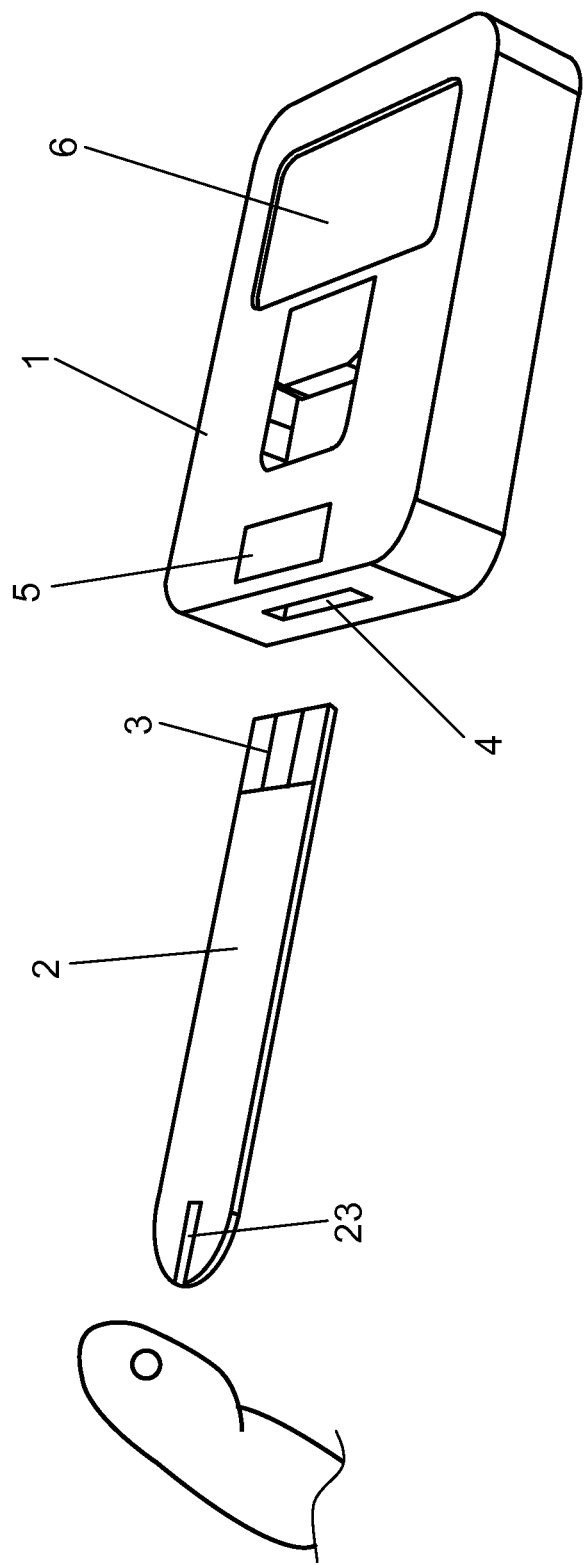
FIG. 1 is a perspective view of a biological information measurement device according to a first exemplary embodiment of the present invention.

As shown in FIG. 1, sensor mounting unit 4, into which electrode unit 3 of sensor 2 typifying a blood glucose level sensor which is, for example, an example of a biological information measurement sensor is inserted, is provided at a front of body case 1. In addition, power source button 5 and display unit 6 are provided on a top surface of body case 1.

FIG. 2 is a control block diagram of the biological information measurement device according to the first exemplary embodiment. Measurement unit 7 is connected to sensor mounting unit 4, and is connected to control unit 8. In addition, display unit 6 and power source cutoff timer circuit 9 are connected to control unit 8.

Further, power source enabling unit 10 is provided in control unit 8, and is connected to power source switch drive circuit 11. Sensor mounting unit 4 is connected to power source switch drive circuit 11 via one-shot pulse circuit 12.

Sensor mounting unit 4 and power source button 5 are connected to power source 13 including a rechargeable battery which is an example of a power source. With power source 13, a user can carry body case 1. As power source 13, the rechargeable battery (so-called secondary battery) is used, but a primary battery such as a button battery or a dry cell battery may be used.

Further, power source 13 is connected to power source switch drive circuit 11 via power source button 5. Power source switch 14 is interposed on a current-carrying circuit between control unit 8 and power source 13 supplying power to control unit 8.

That is, power source switch drive circuit 11 is driven by an input via any one of power source button 5 and one-shot pulse circuit 12 to open and close power source switch 14. The driving operation will be described later in detail.

Figure 3A:
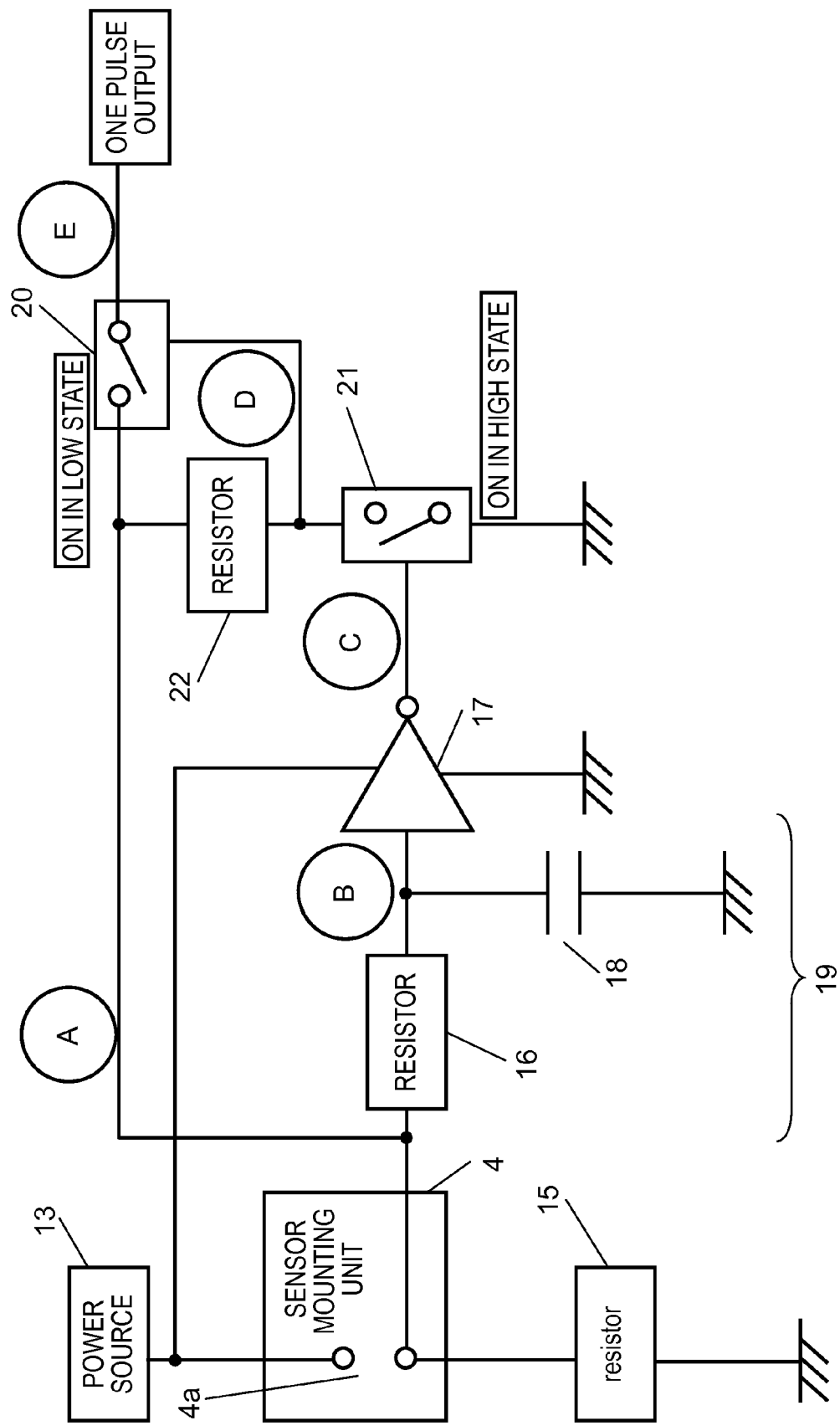
FIG. 3A is an electric circuit diagram of the biological information measurement device according to the first exemplary embodiment of the present invention.

FIG. 3A is an electric circuit diagram of an essential part including one-shot pulse circuit 12 of the biological information measurement device according to the first exemplary embodiment.

As shown in FIG. 3A, resistor 15 is connected between sensor mounting unit 4 and ground. An input side of inverter 17 is connected to sensor mounting unit 4 via resistor 16. Capacitor 18 is connected between resistor 16 and the input side of inverter 17, and is connected to the ground. Capacitor 18 and resistor 16 configure one pulse timer circuit 19.

Further, power source switch drive circuit 11 in FIG. 2 is connected via switch 20 between resistors 15 and 16.

Power source 13 is connected to inverter 17 for power supply. Switch 21 is connected to an output side of inverter 17. One terminal of switch 21 is connected to the ground, and the other terminal thereof is connected via resistor 22 between resistors 15 and 16.

Resistor 22 and switch 21 are connected to switch 20 to drive switch 20.

As shown in FIG. 2, in the above configuration, to drive control unit 8 in FIG. 2, power source button 5 is pressed to drive power source switch drive circuit 11, so that power source switch 14 is closed to thereby drive control unit 8. Thereafter, power source enabling unit 10 in control unit 8 continuously drives power source switch drive circuit 11. Therefore, power source switch drive circuit 11 maintains power source switch 14 in closed state to continuously supply power from power source 13 to control unit 8.

In this exemplary embodiment, other than pressing of power source button 5, sensor 2 is mounted into sensor mounting unit 4 to supply power from power source 13 to control unit 8. This will be described below in detail.

Firstly, when sensor 2 is mounted into sensor mounting unit 4 (step S1 in FIG. 5), sensor detection switch 4a provided in sensor mounting unit 4 is short-circuited via electrode unit 3. As shown in FIG. 4, one-shot pulse circuit 12 which has detected the short-circuit outputs only once a one pulse signal, then the one pulse signal drives power source switch drive circuit 11.

This will be specifically described with reference to FIGS. 3A and 3B. At the time of outputting the one pulse signal from one-shot pulse circuit 12, as indicated by waveform A shown in FIG. 3B, a voltage obtained by resistor 15 of one-shot pulse circuit 12 is outputted via switch 20 to power source switch drive circuit 11. This drives power source switch drive circuit 11, so that as in the above described case that power source button 5 is turned on, power source switch 14 is closed to supply power from power source 13 to control unit 8 via power source switch 14. Thereafter, power source switch drive circuit 11 is maintained in driven state by power source enabling unit 10 in control unit 8.

That is, power source switch drive circuit 11 is configured of an OR circuit which is driven when there is an input via any one of power source button 5 and one-shot pulse circuit 12.

Figure 3B:
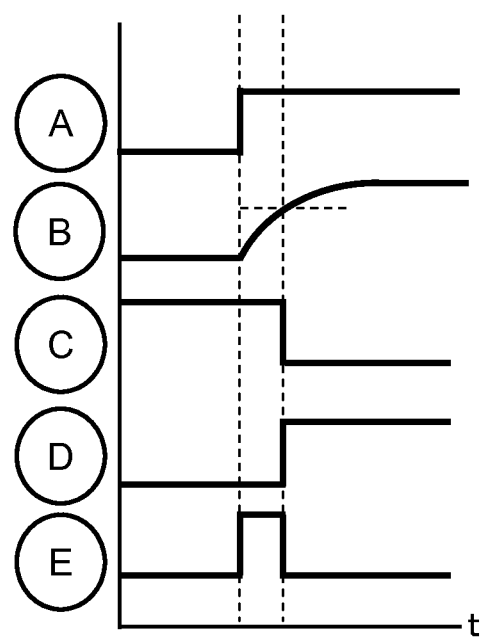
FIG. 3B is a signal waveform chart of an essential part of the biological information measurement device according to the first exemplary embodiment of the present invention.

In this state, as indicated by waveform B in FIG. 3B, an electric potential of capacitor 18 is gradually increased to exceed a voltage set by inverter 17, and thus as indicated by waveform C in FIG. 3B, an output of inverter 17 is cut off. Then, switch 21 is opened so that as indicated by waveform D in FIG. 3B, a voltage between switch 21 and resistor 22 is increased to thereby turn off switch 20. That is, as indicated by waveform E in FIG. 3B, one-shot pulse circuit 12 outputs an one pulse output in which power source switch drive circuit 11 is turned on only during the time in which sensor 2 is mounted into sensor mounting unit 4 to operate one pulse timer circuit 19 (step S2 in FIG. 5).

Figure 5:
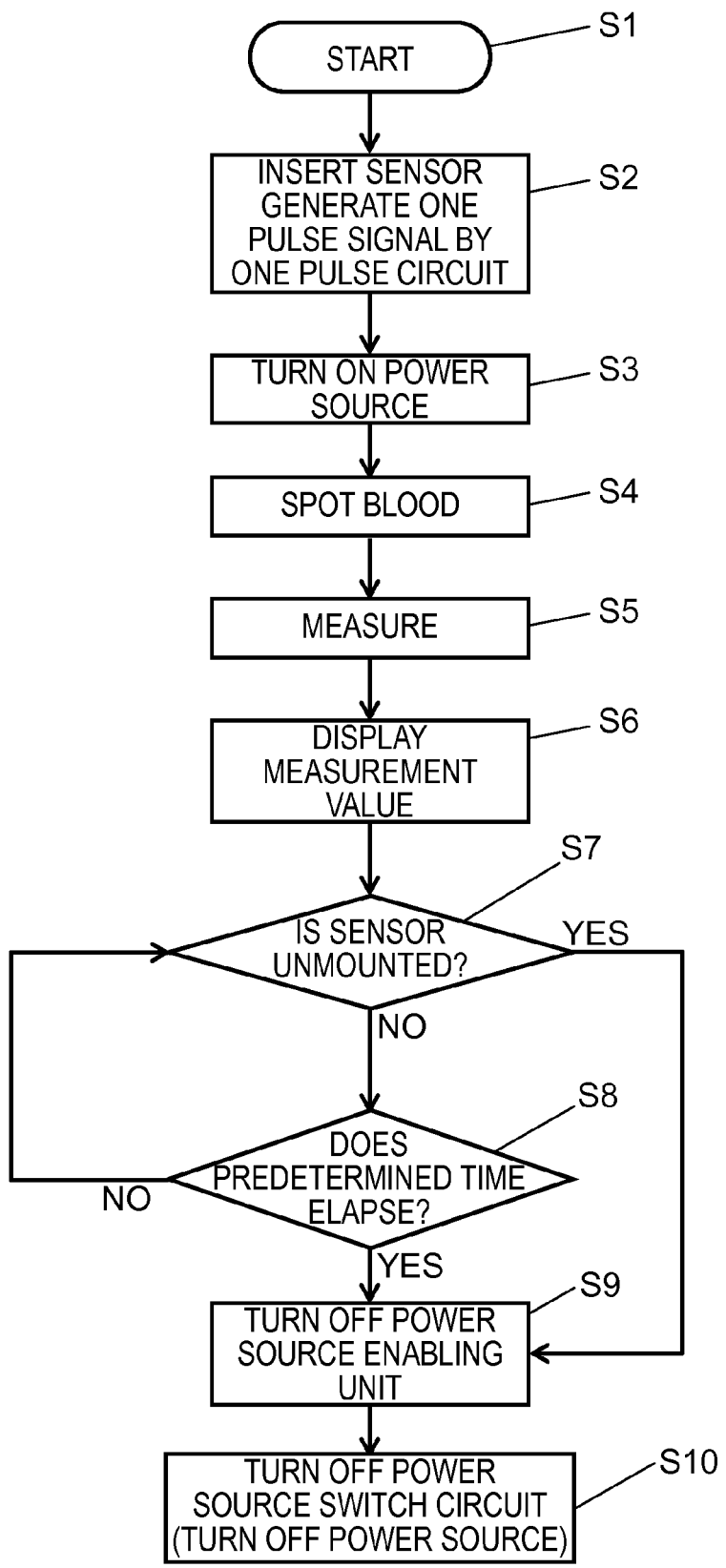
FIG. 5 is a flowchart of an operation of the biological information measurement device according to the first exemplary embodiment of the present invention.

However, when control unit 8 is driven even with such a one pulse input, power source enabling unit 10 in control unit 8 is operated so that power source switch drive circuit 11 can be maintained in on state (step S3 in FIG. 5).

FIG. 4 is an operation explanatory view of an essential part of the biological information measurement device according to this exemplary embodiment illustrating the state in which sensor 2 is mounted into sensor mounting unit 4 to automatically cut off power source 13.

FIG. 4 also shows the state in which sensor 2 is inserted into sensor mounting unit 4 to be continuously mounted thereinto.

At this time, when one-shot pulse circuit 12 outputs the above one pulse output (waveform E in FIG. 3B), power source enabling unit 10 in control unit 8 is continuously in on state.

In this state, when blood is spotted onto spotting unit 23 of sensor 2 shown in FIG. 1 (step S4 in FIG. 5), for example, a blood glucose level is measured by measurement unit 7 (step S5 in FIG. 5) to be displayed on display unit 6 (step S6 in FIG. 5).

In this exemplary embodiment, for instance, after measurement of the blood glucose level, power source cutoff timer circuit 9 which has received a signal from control unit 8 starts its operation. Even when sensor 2 is continuously mounted into sensor mounting unit 4, when predetermined timer time T (for example, 5 minutes to 10 minutes) in power source cutoff timer circuit 9 elapses, power source enabling unit 10 in control unit 8 turns off the signal to power source switch drive circuit 11. Therefore, an output of power source switch drive circuit 11 configured of the OR circuit is turned off (steps S7 to S10 in FIG. 5).

That is, as described above, other than the case that power source button 5 is turned on, when sensor 2 is mounted into sensor mounting unit 4, the output of power source switch drive circuit 11 is turned on. Only when power source button 5 is turned on, the output of power source switch drive circuit 11 is turned on.

Further, in the same manner as power source button 5, only when sensor 2 is mounted into sensor mounting unit 4, one-shot pulse circuit 12 is turned on, as indicated by waveform E in FIG. 3B. Thereafter, power source enabling unit 10 in control unit 8 maintains the output of power source switch drive circuit 11 in on state.

Therefore, as described above, when predetermined timer time T (for example, 5 minutes to 10 minutes) in power source cutoff timer circuit 9 elapses, power source enabling unit 10 in control unit 8 turns off the signal to power source switch drive circuit 11. Therefore, as shown in FIG. 4, the output of power source switch drive circuit 11 configured of the OR circuit is turned off. Then, power source switch 14 is opened to be turned off so that power supplied from power source 13 to control unit 8 is completely cut off.

As a result, even when sensor 2 is continuously mounted into sensor mounting unit 4, power is not supplied from power source 13 to control unit 8, so that unintended power consumption can be prevented.

As described above, in the biological information measurement device according to this exemplary embodiment, as indicated by waveform E in FIG. 3B, only when sensor 2 is mounted into sensor mounting unit 4, one-shot pulse circuit 12 is turned on to turn on power source switch drive circuit 11. Thereafter, power source enabling unit 10 in control unit 8 maintains power source switch drive circuit 11 in on state.

That is, when sensor 2 is mounted into sensor mounting unit 4, the one pulse signal of one-shot pulse circuit 12 is outputted to power source switch drive circuit 11 only once. Therefore, after the output, a mounted state of sensor 2 cannot affect power source switch drive circuit 11.

Therefore, even when sensor 2 is continuously mounted into sensor mounting unit 4 after measurement of biological information including the blood glucose level, when predetermined timer time T (for example, 5 minutes to 10 minutes) in power source cutoff timer circuit 9 elapses, power source enabling unit 10 in control unit 8 turns off the signal to power source switch drive circuit 11. Therefore, as shown in FIG. 4, the output of power source switch drive circuit 11 configured of the OR circuit is turned off. Then, power source switch 14 is opened to be turned off.

This can completely cut off power supplied from power source 13 to control unit 8. That is, power cannot be supplied to the DC-DC converter (not shown) in control unit 8.

As a result, power is not supplied from the power source to the control unit, so that unintended power consumption can be prevented from occurring.

Therefore, in this exemplary embodiment, the device in which the user can carry body case 1 with power source 13 including the rechargeable battery is very effective since power source 13 including the rechargeable battery can have a long life.

In this exemplary embodiment, power source enabling unit 10 is provided in control unit 8 to connect power source enabling unit 10 to power source switch drive circuit 11, but power source enabling unit 10 may be provided outside control unit 8.

More specifically, power source enabling unit 10 may be provided between control unit 8 and power source switch drive circuit 11 (not shown). In this configuration, control unit 8 uses power source enabling unit 10 to drive power source switch drive circuit 11.

As described above, in this exemplary embodiment, one-shot pulse circuit 12 is interposed between sensor mounting unit 4 and power source switch drive circuit 11, and when sensor 2 is mounted into sensor mounting unit 4, one-shot pulse circuit 12 outputs the one pulse signal to power source switch drive circuit 11 only once. The one pulse signal drives power source switch drive circuit 11 to turn on power source switch 14 interposed between control unit 8 and power source 13 so that power supply from power source 13 to control unit 8 is started.

When sensor 2 is mounted into sensor mounting unit 4, the one pulse signal is outputted to the power source switch drive circuit only once. Therefore, after the one pulse signal is outputted, a mounted state of sensor 2 cannot affect power source switch drive circuit 11.

Therefore, even when sensor 2 is left mounted into sensor mounting unit 4 after measurement of the blood glucose level, power source switch drive circuit 11 can automatically turn off power source switch 14. This can completely cut off power supplied from power source 13 to control unit 8. That is, unlike the conventional sleep mode, power cannot be continuously supplied to the DC-DC converter (not shown) in control unit.

As a result, power is not supplied from power source 13 to control unit 8, so that unintended power consumption can be prevented from occurring.

INDUSTRIAL APPLICABILITY

It is expected that the present invention can be widely used as the biological information measurement device for measuring biological information, such as a blood glucose level, from blood.

REFERENCE MARKS IN THE DRAWINGS 1 body case
2 sensor (an example of a biological information measurement sensor)
3 electrode unit
4 sensor mounting unit
4a sensor detection switch
5 power source button
6 display unit
7 measurement unit
8 control unit
9 power source cutoff timer circuit
10 power source enabling unit
11 power source switch drive circuit
12 one-shot pulse circuit
13 power source
14 power source switch
15, 16, 22 resistor
17 inverter
18 capacitor
19 one pulse timer circuit
20, 21 switch
19 spotting unit
23 spotting unit

The invention claimed is:
1. A biological information measurement device comprising:
 a body case having a sensor mounting unit;
 a measurement unit connected to the sensor mounting unit;
 a control unit connected to the measurement unit;
 a power source supplying power to the control unit;
 a power source switch interposed between the control unit and the power source; and
 a power source switch drive circuit connected to the sensor mounting unit,
 wherein a one-shot pulse circuit is interposed between the sensor mounting unit and the power source switch drive circuit, and wherein the power source switch drive circuit, which is driven by an output of the one-shot pulse circuit, opens and closes the power source switch.

2. The biological information measurement device according to claim 1, wherein the power source switch drive circuit drives the power source switch to connect the control unit and the power source when a sensor is mounted into the sensor mounting unit.

3. The biological information measurement device according to claim 1, wherein the control unit is provided with a power source enabling unit connected to the power source switch drive circuit.

4. The biological information measurement device according to claim 3, wherein the power source switch drive circuit includes an OR circuit.

5. The biological information measurement device according to claim 1, wherein the one-shot pulse circuit includes: a one pulse timer circuit connected to the sensor mounting unit and an inverter connected to the one pulse timer circuit.

* * * * *